US009999363B2

(12) United States Patent
Shah et al.

(10) Patent No.: US 9,999,363 B2
(45) Date of Patent: Jun. 19, 2018

(54) SYSTEM AND METHOD FOR NEURAL INTERFACE WITH MODULAR ACTIVE ELECTRONICS

(71) Applicant: Lawrence Livermore National Security, LLC, Livermore, CA (US)

(72) Inventors: Kedar G. Shah, San Francisco, CA (US); Sarah H. Felix, Oakland, CA (US); Satinderpall S. Pannu, Pleasanton, CA (US); Vanessa Tolosa, Oakland, CA (US); Angela C. Tooker, Dublin, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 515 days.

(21) Appl. No.: 14/684,673

(22) Filed: Apr. 13, 2015

(65) Prior Publication Data
US 2016/0296130 A1 Oct. 13, 2016

(51) Int. Cl.
*A61N 1/04* (2006.01)
*A61B 5/04* (2006.01)
*A61N 1/05* (2006.01)
*A61N 1/378* (2006.01)
*A61N 1/372* (2006.01)
*A61B 5/00* (2006.01)

(52) U.S. Cl.
CPC ........ *A61B 5/04001* (2013.01); *A61N 1/0551* (2013.01); *A61N 1/3787* (2013.01); *A61N 1/37211* (2013.01); *A61N 1/37229* (2013.01); *A61B 5/002* (2013.01); *A61B 2560/0214* (2013.01); *A61B 2560/045* (2013.01); *A61B 2562/166* (2013.01)

(58) Field of Classification Search
CPC ............... A61B 5/002; A61B 5/04001; A61B 2560/0214; A61B 2560/045; A61B 2562/166; A61N 1/0551; A61N 1/37211; A61N 1/37229; A61N 1/3787
USPC .... 600/372, 373, 377, 378, 382, 393; 607/2, 607/115, 149, 152
See application file for complete search history.

(56) References Cited

U.S. PATENT DOCUMENTS

2006/0173263 A1* 8/2006 He ..................... A61B 5/04001
600/378
2014/0163348 A1* 6/2014 Kim ..................... A61N 1/0551
600/377

FOREIGN PATENT DOCUMENTS

CN    102178999 A    9/2011
KR    101500653 B1   3/2015
WO    2012100258 A2  7/2012

OTHER PUBLICATIONS

International Search Report and Written Opinion issued Jul. 11, 2016 in corresponding PCT Application No. PCT/US2016/027260.

* cited by examiner

*Primary Examiner* — Michael Carey
(74) *Attorney, Agent, or Firm* — Harness, Dickey & Pierce, PLC

(57) ABSTRACT

A modular, high density electrical system is disclosed which makes use of an interface component, which is well suited to being placed in contact with an anatomy of either a human or an animal, and which may be releasably coupled to an electronics module subsystem. The interface component has a plurality of electrically conductive interconnect pads that may be releasably secured by a member to a plurality of electrically conductive pads of the electronics module subsystem. The electronics module subsystem may have a substrate which supports both an electronics circuit and the interconnect pads.

22 Claims, 8 Drawing Sheets

SYSTEM AND METHOD FOR NEURAL INTERFACE WITH MODULAR ACTIVE ELECTRONICS

STATEMENT OF GOVERNMENT RIGHTS

The United States Government has rights in this invention pursuant to Contract No. DE-AC52-07NA27344 between the U.S. Department of Energy and Lawrence Livermore National Security, LLC, for the operation of Lawrence Livermore National Laboratory.

FIELD

The present disclosure relates to electrical monitoring and/or recording systems, and more particularly to a high-channel count electrical recording system with active electronics that is especially well suited for medical, surgical, neuroscience and research applications where a large number of independent electrical signals need to be monitored within tight space restrictions.

BACKGROUND

The statements in this section merely provide background information related to the present disclosure and may not constitute prior art.

For advanced neural recordings, there is a growing need for neural interfaces with a large number of independent channels to be able to record complex neural signals. State-of-art approaches utilize neural interfaces with typically 1-128 channels, and each channel is connected to an external electronics system using a single wire (or trace, or electrical conduit). As the number of channels increase, the space necessary for individual wires can become unmanageable and/or impractical for in vivo use.

In order to make high-channel count neural recordings less cumbersome, recent efforts have been devoted to using multiplexing electronics that can combine the signals from multiple channels into a single shared stream. Additionally, multiplexing can be combined with signal amplification, filtering, and signal conditioning strategies to help further reduce the physical size of an electronic module being used to receive the signals from multiple channels.

One specific approach to solving the issue of receiving a large number of independent signal streams being with one electronic module or subsystem is channels using a combined neural interface with active circuitry. In this approach, the neural interface is combined with the active circuitry. This is achieved by fabricating the entire probe and electronics simultaneously. Though the electrical performance of such devices is high, the cost of fabrication increases significantly as wafer real-estate is used for the large footprint of the neural interface. Additionally, if surgical error damages the probe, the entire system needs to be disposed, which adds to cost of this approach. Finally, the yield of such devices is often low, since the performance of the neural interface and electronics are linked. In effect, if either component malfunctions, the entire system needs to be disposed. Bench-top testing of such systems is also difficult since there is no way to interface with individual channels of the neural interface.

Another approach is using active circuitry which is assembled onto a neural interface. With this approach, electronics are permanently assembled onto the neural interface using semiconductor assembly techniques. Though the cost of electronics can be reduced by de-coupling it from device fabrication, the overall cost of assembly is still high. Once assembled, the entire system needs to be disposed of in the event of surgical error. Additionally, it is difficult to independently verify the functionality of the neural interface prior to permanent bonding to the electronics. Upon assembly, if the device is found to be non-functional, the entire system must be disposed of.

Still another approach is using an active electronics headstage. With this approach, the active electronics are kept separate from the neural interface. The active electronics are assembled onto a printed circuit board with a connector leading to the device and another connector leading to the acquisition electronics. A mating standard connector is attached to the neural interface. This allows for the researcher to use multiple designs or iterations of devices with the same active electronics headstage. The disadvantage of this approach is that standard connectors are extremely low density and hence the total number of channels that are practical for most studies is limited to about 32.

SUMMARY

In one aspect the present disclosure relates to a modular, high density electrical system. The system may comprise an interface component having a flexible substrate and a plurality of independent, electrically conductive elements disposed on the substrate. The electrically conductive elements may be in communication with a plurality of electrically conductive interconnect pads which are also disposed on the substrate. An electronics module subsystem, independent of the interface, may be included which has a substrate, an electronics circuit supported on the substrate, and a plurality of electrically conductive pads in electrical communication with the electronics circuit. The interface component may be of dimensions enabling a portion thereof having the electrically conductive interconnect pads to be positioned in electrical contact with the electrically conductive pads of the interconnect subassembly. A member may be included for releasably holding the electrically conductive interconnect pads in contact with the electrically conductive pads of the electronics module subsystem.

In another aspect the present disclosure relates to a modular, high density electrical data acquisition system comprising a neural interface component having a flexible substrate and a plurality of independent, electrically conductive elements disposed on the substrate within a first region of the flexible substrate. A plurality of electrically conductive traces may be formed on the flexible substrate and in communication with the electrically conductive elements. A plurality of electrically conductive interconnect pads may be formed in an array on the substrate within a second region, and may be in communication with the plurality of electrically conductive traces. An electronics module subsystem may also form a portion of the system and may be independent of the neural interface component. The electronics module subsystem may include a substrate and an electronics circuit supported on the substrate. The substrate may also include a plurality of electrically conductive pads in electrical communication with the electronics circuit. The plurality of electrically conductive pads may be configured in accordance with the array of the electrically conductive interconnect pads. An independent interconnect subassembly may be included which is configured to be positioned between the neural interface component and the electronics module subsystem, and to facilitate non-permanent electrically conductive connections between the array of electrically conductive interconnect pads and the electrically conductive pads when the second region of the neural interface component is aligned over the electrically conductive pads. A member may be included for assisting in clamping the second region of the neural interface component and the independent interconnect subassembly adjacent the substrate of the electronics module subsystem.

In still another aspect the present disclosure relates to a method for at least one of obtaining or generating electrical signals. The method may comprise providing an interface component having a flexible substrate and a plurality of independent, electrically conductive elements disposed on the substrate. The electrically conductive elements may be formed so as to be in communication with a plurality of electrically conductive interconnect pads, which are also disposed on the substrate. The electrically conductive elements may be used to at least one of receive or to generate the electrical signals when the interface component is placed in contact with matter. The electrically conductive interconnect pads of the interface component may be releasably secured to a plurality of electrically conductive pads of an electronics module subsystem. An electrical circuit contained in the electronics module subsystem may then be used to receive the electrical signals.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

DETAILED DESCRIPTION

Figure 1:
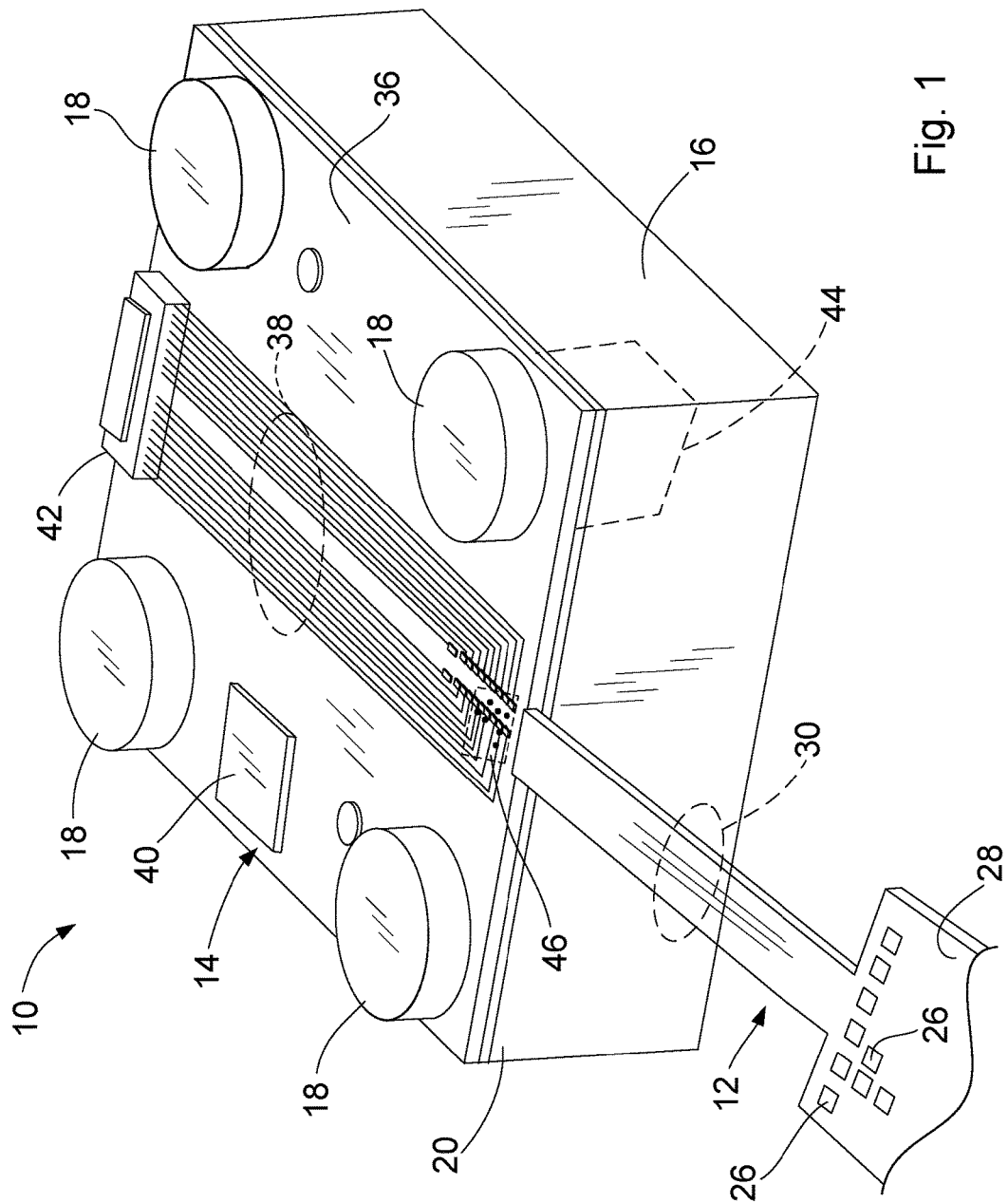
FIG. 1 is a simplified perspective view of one embodiment of a neural interface system having a modular active electronics module.

The following description is merely exemplary in nature and is not intended to limit the present disclosure, application, or uses. It should be understood that throughout the drawings, corresponding reference numerals indicate like or corresponding parts and features.

Figure 2:
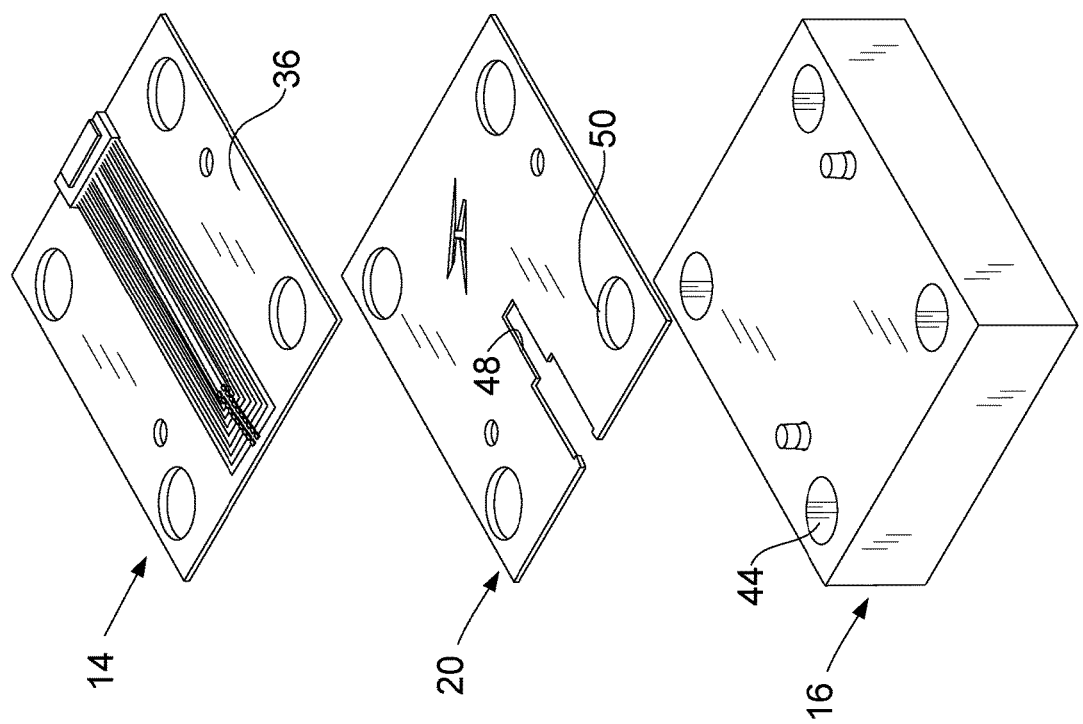
FIG. 2 is an exploded perspective view of the components of the system of FIG. 1.

Referring to FIGS. 1 and 2, there is shown an interface system 10 in accordance with one embodiment of the present disclosure. While the interface system 10 in this example forms a "neural" interface system, and may be referred to throughout the following discussion as a "neural" interface system, it will be appreciated that the system 10 is not limited to applications involving sensing neural electrical signals. The system 10 is expected to find utility in connection with neural sensing applications where chemical signals are sensed and cause a sensor to generate an electrical signal in response to the presence of a chemical signal, as well as to bio-sensing applications as well. The system 10 further is expected to find utility in applications where it necessary or desirable to obtain electrical signals from some form of matter, or apply electrical stimulation signals to some form of matter. In one application the matter may be any human or animal anatomy. Other applications could involve non-anatomical applications where the application requires the sensing of electrical signals or chemical signals, or the application involves bio-sensing. Thus, the system 10 is not limited to use only in connection with applications involving the sensing of neural signals associated with animals or humans.

The system 10 in this example may include a neural interface component 12 which is releasably clamped to an electronics module subsystem 14 via a clamping member 16 and fastening elements 18. subassembly. Optionally, a shim 20 may be positioned between the clamping member 16 and the electronics module subsystem 14. With brief reference to FIGS. 3 and 4, the system 10 may also include an independent interconnect subassembly 22 which may be used to help ensure electrical contact between the neural interface component 12 and the electronics module subsystem 14.

Figure 5:
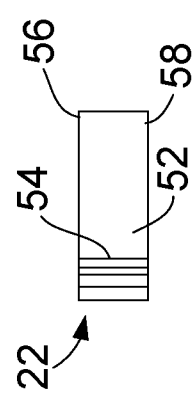
FIG. 5 is an end view of the interconnect subassembly of FIG. 4.

With specific regard to FIGS. 1 and 5, the neural interface component 12 can be seen in greater detail. It is a principal advantage of the system 10 that the neural interface component is releasably secured (i.e., clamped) to the electronics module subsystem 14. As such, if the neural interface component is damaged during use it can be easily detached without any special tools or complex disassembly procedures, and a new neural interface component attached to the electronics module subsystem 14. Obviously, another important benefit is if the shape or configuration of the neural interface is needed for a specific application, another neural interface component 12 with the needed shape/configuration can be attached to the electronics module subsystem 14. This enables the system 10 to be better customized for use in connection with a wide variety of anatomical applications, both on human anatomy and on the anatomies of different types of animals.

Figure 6:
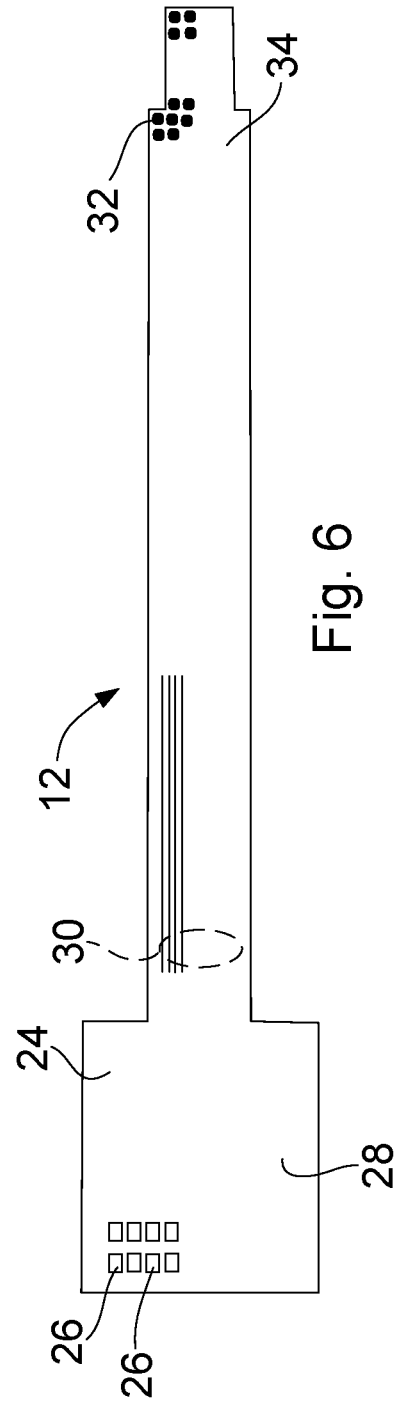
FIG. 6 is a plan view of the neural interface component.

The neural interface component 12, as shown in FIGS. 1 and 6, includes a substrate 24 which may be made from silicon or any other suitable flexible polymer. The substrate 24 includes a plurality of independent, electrically conductive elements 26 supported on the substrate 24 within a first region 28 of the substrate 24, and plurality of circuit traces 30 in communication with the electrically conductive elements 26, and a plurality of electrically conductive interconnect pads 32 in communication with the electrically conductive elements 26. The electrically conductive interconnect pads 32 are disposed within a second region 34 of the substrate 24 and are configured in an array having a predetermined shape. The electrically conductive elements 26 essentially form electrodes that may be used to collect electrical signals from human or animal anatomy, or to deliver electrical signals for the purpose of stimulating specific designated areas of a human or animal anatomy. The electrically conductive elements 26 may be configured in any suitable array configuration with virtually any desired spacing. Thus, the depiction of the electrically conductive elements 26 in a generally square shape in FIG. 6 is merely intended to illustrate one specific example of a configuration that the elements 26 may take.

The electrically conductive interconnect pads 32 may be configured in a much more densely packed configuration, as noted in FIG. 5. The more densely packaged configuration of the electrically conductive interconnect pads 32 helps to maintain a very condensed "footprint", which in turn helps to maintain the overall size of the electronics module subsystem 14 very small.

Figure 3:
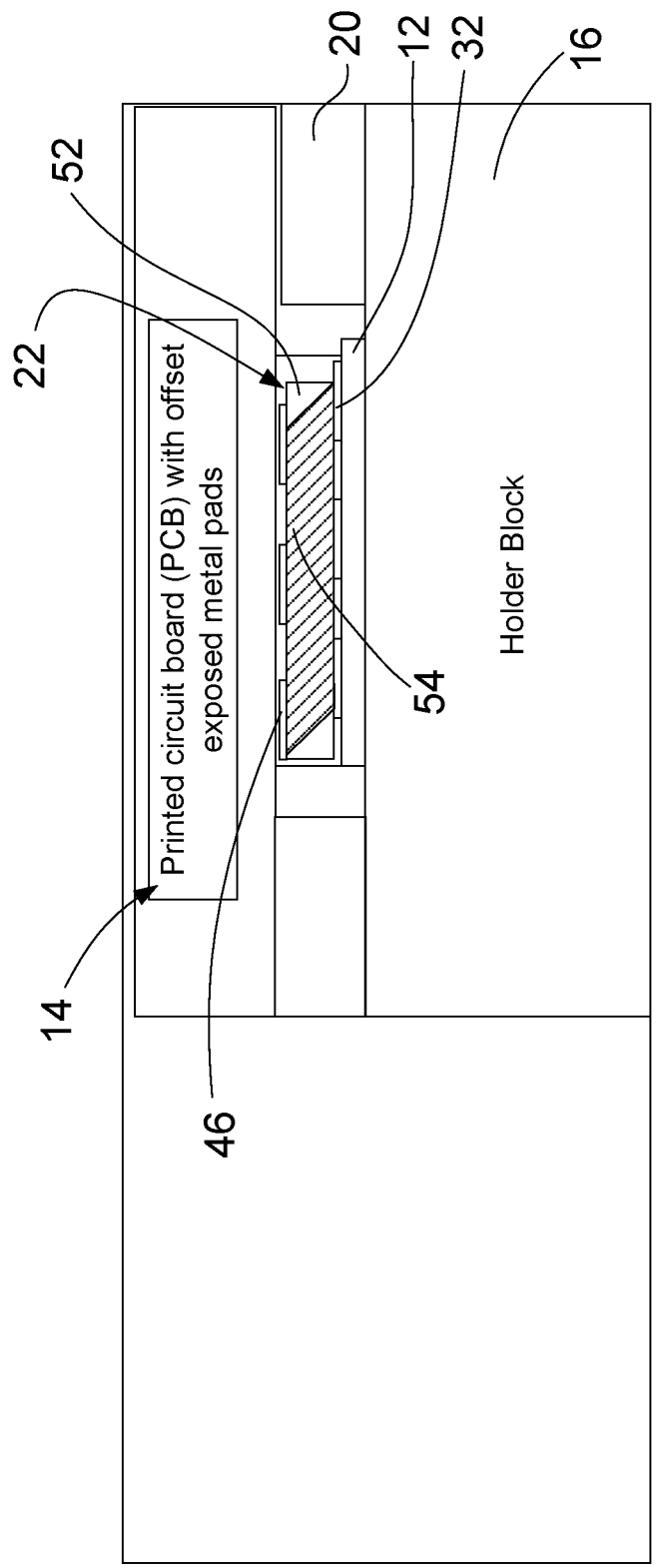
FIG. 3 is a highly simplified side cross sectional view showing an interconnect subassembly sandwiched between electrically conductive metallic pads associated with an electronics module subsystem and a clamping member.

With further reference to FIGS. 1 and 3, the electronics module subsystem 14 may include a substrate 36 on which is disposed a plurality of circuit traces 38. The circuit traces 38 are in electrical communication with a plurality of an electronics circuit 40 and an electrical connector 42. Electronics circuit 40 may include one or more of a multiplexer, a processor, a circuit for generating electrical stimulation signals to be applied to a human or animal anatomy, a microprocessor or controller, a memory such as RAM and/or ROM, filtering circuitry, and wireless or wired communication circuitry. A miniature battery may also be included along with a charging port, or alternatively suitable circuitry to enable wireless (e.g., inductive) charging may be included as well. Preferably If wireless communication circuitry is employed, such circuitry may include a Bluetooth® communications protocol, miniature wireless communications transceiver. The connector 42 enables the entire system 10 to be connected to an external system, for example a data acquisition system, computer or other electronic device. Connector 42 may take any suitable form such as, without limitation, an RS-232 connector, an RS-422 connector, etc. The electronics circuit 40 and its various components are preferably hermetically sealed.

FIG. 1 also illustrates fastening elements 18 which are used to engage the clamping member 16 for the purpose of clamping the neural interface component 12 to the electronics module subsystem 14. The fastening elements 18 in this example may be threaded fasteners which engage with threaded openings 44 in the clamping member 16. However, virtually any other type of fastening structure may be used as long as maintains the interface subassembly. Optionally, the neural interface component 12 itself could incorporate a permanently attached, rigid portion of material that effectively clamps the second region 34 thereof to the substrate when secured by suitable fastening elements. Optionally, independent spring loaded clamps may be used for securing the clamping member 16. Still further, the means for clamping could be accomplished using virtually any form of mechanical, magnetic, or chemical components or substances (e.g., a bonding agent/adhesive). The clamping mechanism may also include at least one seal, such as an O-ring, to protect the interconnection region from moisture ingress.

With further reference to FIGS. 1 and 2, the substrate 36 of the electronics module subsystem 14 also includes a plurality of independent, electrically conductive pads 46 in communication with the circuit traces 38, and thus being in communication with the electronics circuit 40. The electrically conductive pads 46 are arranged in a predetermined array or configuration such that the electrically conductive interconnect pads 32 in the second region 34 of the neural interface component 12 will lay over, and be in direct contact with the conductive pads 46, when the second region 34 is clamped between the clamping member 16 and the substrate 36 of the electronics module subsystem 14. Thus it will be appreciated that each one of the electrically conductive elements 26 on the neural interface component 12 will be in electrical communication with a specific one of the electrically conductive pads 46.

As noted in FIG. 2, the shim 20 may have a cutout section 48 to accommodate the second region 34 of the neural interface component 12 as well as the interconnect subassembly 22. Additional holes 50 may be included to allow portions of the fastening elements 18 to pass therethrough.

Figure 4:
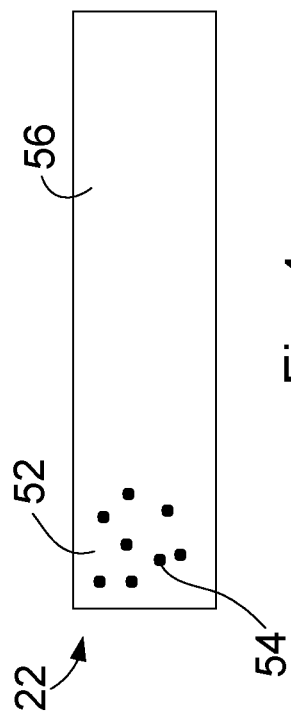
FIG. 4 is a highly simplified plan view of the interconnect subassembly.

With further reference to FIGS. 3, 4, and 5, the interconnect subassembly 22 may have a substrate 52 made from silicone or any other suitable polymer which is flexible and/or slightly compressible, as well as electrically insulative. The substrate 52 may have embedded therein a plurality of densely packed, short lengths of electrically conductive (e.g., copper) wires 54 that are exposed on opposing planar surfaces 56 and 58 of the substrate 52. The wires 54 are embedded such that they are not in contact with one another within the substrate 52, and such that they extend either generally perpendicularly to the surfaces 56 and 58 or at a slight angle thereto. The wires 54 may be have a diameter of about 0.0005-0.005 inch (0.0127-0.127 mm), and hundreds or even thousands or more such wires may be densely packed into the substrate 52. When the interconnect subassembly 22 is clamped between the electrically conductive interconnect pads 32 and the electrically conductive pads 46, they help to ensure excellent electrical connectivity between the pads 32 and 46. Those ones of the exposed opposing ends of the wires 54 that are not in contact with both of the pads 32 or 46 have no effect on operation of the system 10. The thickness of the shim 48 is preferably such that it enables the substrate 56 of the interconnect subassembly 22 to be compressed slightly when the electronics module subsystem 14 is clamped over the subassembly 22 and the neural interface component 12. This ensures excellent electrical contact between the wires 54 and the pads 32 and 46.

Figure 7:
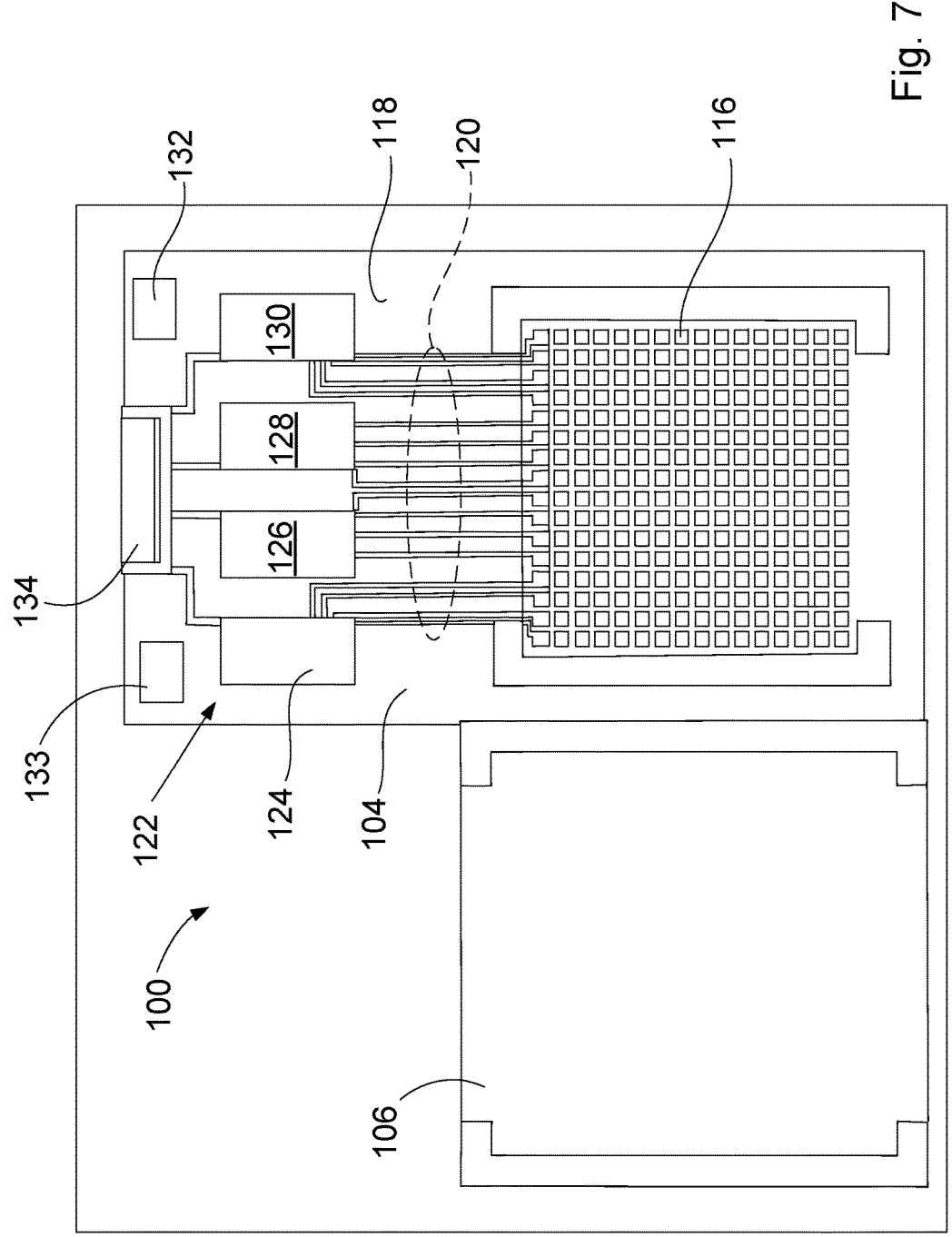
FIG. 7 is a plan view of another embodiment of a system in accordance with the present disclosure.
Figure 8:
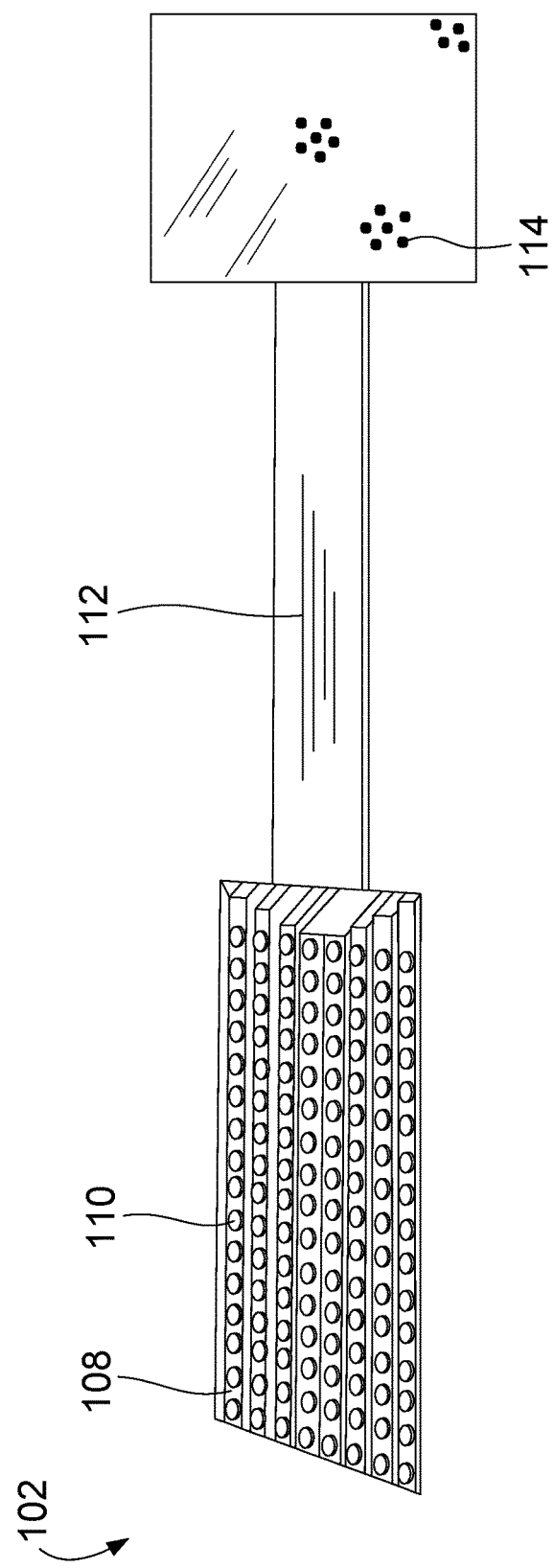
FIG. 8 is a plan view of a neural interface component for use with the components shown in FIG. 7.

Referring to FIGS. 7-8, another embodiment of a system 100 in accordance with the present disclosure is shown. The system 100 in FIGS. 7-8 is somewhat similar in construction to the system 10 and includes a neural interface component 102 (FIG. 8), an electronics module subsystem 104 and a clamping member 106. The interconnect subassembly 22 of FIGS. 3-5 may be used with the system 100, although if the neural interface component 102 is suitably constructed with sufficient flexibility and/or a slight degree of compressibility of its substrate, the interconnect subassembly 22 may not be required.

The neural interface component 102 (FIG. 8) is similar in construction to the neural interface component 12 and includes a substrate 108 having an array of independent electrically conductive elements 110 configured in a desired overall geometric shape. In FIG. 8 the electrically conductive elements 110 are arranged in a generally rectangular configuration, although virtually any configuration is possible. The needs of specific applications and the specific anatomical structures to which the neural interface component 102 will be attached will heavily dictate the desired overall configuration of the array of elements 110.

The electrically conductive elements 110 are electrically coupled via circuit traces 112 to a plurality of independent electrically conductive interconnect pads 114. In this example the array of the interconnect pads 114 is configured in a generally square shape. The substrate 108 is preferably made of silicon or another flexible polymer, and may also be constructed to impart a slight degree of compressibility.

With further reference to FIG. 7, the electronics module subsystem 104 includes a plurality of electrically conductive pads 116 supported on a substrate 118. The electrically conductive pads 116 in this example are arranged in a generally square configuration. Circuit traces 120 electrically couple the electrically conductive pads 116 to an electronics module subsystem 122 which in this example of comprised of a processor 124, a multiplexer 126, a filter 128 and a communications subsystem 130. An optional rechargeable or non-rechargeable battery 132 may also form part of the electronics module subsystem 122. A connector 134 enables the electronic module subsystem 122 to be coupled to an external system such as a computer or data acquisition component. The clamping member 106 may be flipped 180 degrees from its orientation shown in FIG. 7 and secured over the electrically conductive pads 116 by suitable fasteners (not shown) when a portion of the neural interface component 102 is positioned in place over the electrically conductive pads 116. A slightly raised non-conductive wall portion 136 on the substrate 118 and a raised wall portion 138 on the clamping member 106 help to align the clamping member 106 over the electrically conductive pads 116. If the battery 132 is a rechargeable battery, the system 100 may also incorporate an inductive charging circuit to enable the battery to be charged wirelessly from an external current source. Optionally, the connector 134 could provide pins dedicated to receiving a charging current from an external power source. Still further, the various electronics components could be formed within a hermetically sealed subsystem. Still further, the electronics components may include one or more antennas 133 for wireless data and/or power telemetry.

Figure 9:
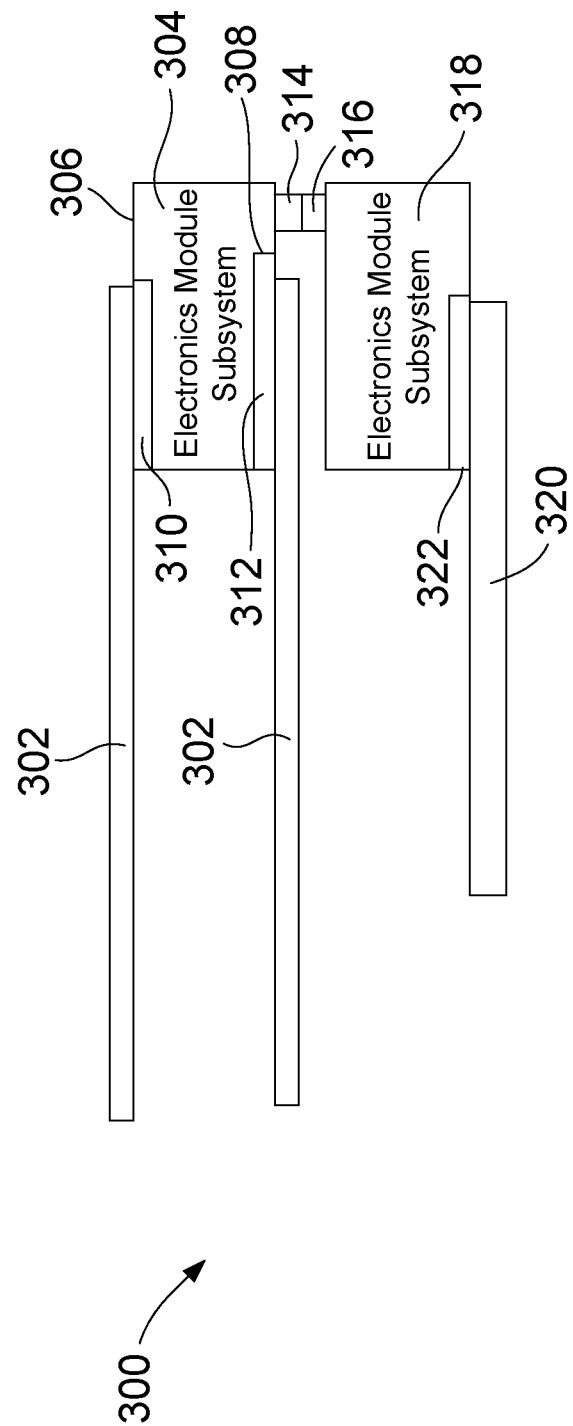
FIG. 9 is a highly simplified side view of a system in accordance with another embodiment of the present disclosure showing how a plurality of neural interface components can be coupled to opposing surfaces of a printed circuit board being used with an electronics module subsystem, and further showing how multiple electronics module subsystems can be daisy chained together if needed.

Referring to FIG. 9, a system 300 is shown to illustrate how a plurality of independent neural interface components 302 can be coupled to opposing surfaces 306 and 308 of a single electronics module subsystem 304. Each of the opposing surfaces 306 and 308 include an array of electrically conductive pads 310 and 312, respectively. Connector 314 may be linked to a connector 316 of another electronics module subsystem 318. Connector 320 of the electronics module subsystem 318 may be used to connect to still another electronics module subsystem. In this manner a plurality of electronic module subsystems may be "daisy chained" together. Electronics module subsystem 318 may have one or more neural interface components 320 coupled to an array of electrically conductive pads 322 carried thereon. By securing one of the neural interface connectors to one surface 306 and the other to the opposing surface 308 of the electronics module subsystem 304, the overall "footprint" or area required on the module subsystem 304 for interfacing the neural interface components 302 thereto is reduced by one-half or more.

Figure 10:
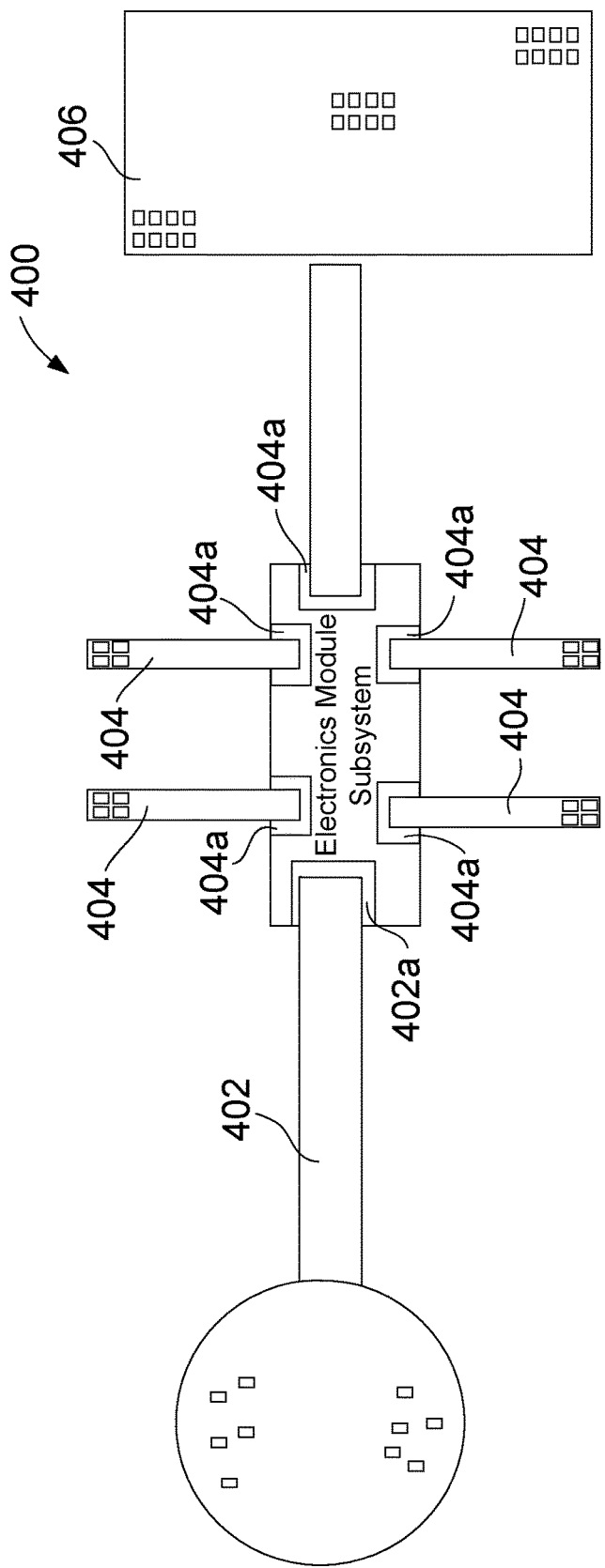
FIG. 10 is a plan view of another embodiment of a system in accordance with the present disclosure illustrating how a plurality of different configurations of neural interface components can be used with a single electronics module subsystem.

FIG. 10 shows still another system 400 in accordance with another optional configuration of the present disclosure. The system 400 in this example makes use of a plurality of neural interface components 402, 404 and 406 404 that are significantly different in configuration and coupled to an electronics module subsystem. In this example neural interface components 404 may be probes which penetrate into human or animal tissue, while components 402 and 406 may be pads that are laid over tissue. Neural interface components 402-406 are configured such that their electrically conductive interconnect pads (not visible in the Figure) interface with electrically conductive pads 402a, 404a and 406a on a substrate 408 of an electronics module subsystem 410. FIG. 10 demonstrates that a large plurality of neural interface components can be attached which each have dramatically different configurations.

The various embodiments disclosed enable a system to be provided in which the neural interface component can be readily replaced when needed. Thus, one electronics module subsystem can be re-used if needed with one or more different neural interface components.

While various embodiments have been described, those skilled in the art will recognize modifications or variations which might be made without departing from the present disclosure. The examples illustrate the various embodiments and are not intended to limit the present disclosure. Therefore, the description and claims should be interpreted liberally with only such limitation as is necessary in view of the pertinent prior art.

What is claimed is:

1. A modular, high density system comprising:
    a interface component having:
        a flexible substrate;
        a plurality of independent, electrically conductive elements disposed on the substrate in communication with a plurality of electrically conductive interconnect pads, also disposed on the substrate;
    an electronics module subsystem independent of the interface component, including:
        a substrate;
        an electronics circuit supported on the substrate;
        a plurality of electrically conductive pads in electrical communication with the electronics circuit;
        the interface component being of dimensions enabling a portion thereof having the electrically conductive interconnect pads to be positioned in electrical contact with the electrically conductive pads; and
        a member for releasably holding the electrically conductive interconnect pads in contact with the electrically conductive pads of the electronics module subsystem.

2. The system of claim 1, wherein the system forms at least one of:
    a data acquisition system for recording at least one of electrical signals; or
    a system for supplying electrical stimulation signals.

3. The system of claim 1, further comprising an interconnector assembly configured to be sandwiched between the electrically conductive pads and the electrically conductive interconnect pads, to assist in forming electrically conductive connections between the electrically conductive pads and the electrically conductive interconnect pads.

4. The system of claim 3, wherein the interconnector assembly includes:
    an insulating material being at least one of flexible and slightly compressible, and forming a generally planar member having opposing generally planar surfaces; and
    a plurality of electrically conductive wires embedded in the insulating material such that portions of each of the wires are exposed on the opposing generally planar surfaces, and thus able to make electrically conductive contact with the electrically conductive interconnect pads and the electrically conductive pads.

5. The system of claim 4, wherein the density of the plurality of electrically conductive wires is greater than the density of the electrically conductive interconnect pads.

6. The system of claim 5, wherein alignment of the interconnector assembly with the electrically conductive pads and the electrically conductive interconnect pads is not critical because of a dense packaging of the electrically conductive wires, and since none one of the electrically conductive wires, when compressed, can bridge a gap between adjacent ones of the electrically conductive interconnect pads.

7. The system of claim 1, wherein the flexible substrate is formed from at least one of a flexible polymer or silicon.

8. The system of claim 1, wherein the electrically conductive elements are formed in a first region of the substrate of the interface component, and the electrically conductive interconnect pads are formed in a second region of the substrate of the interface component.

9. The system of claim 8, further comprising a plurality of circuit traces connecting the electrically conductive elements and the electrically conductive interconnect pads.

10. The system of claim 1, wherein the system includes at least one of the following features:
the electronics circuit comprises a hermetically sealed subsystem;
the electronics module subsystem further includes a connector for enabling an external electrical communications cable to be coupled in communication with the electronics circuit; or
the electronics circuit includes at least one antenna for at least one of wireless data transmission or reception;
the electronics circuit includes at least one antenna for enabling wireless power telemetry.

11. The system of claim 1, wherein the electronics module subsystem is constructed of biocompatible materials suitable for extended contact with a skin layer or implanted into tissue of at least one of a human or an animal.

12. A modular, high density electrical data acquisition system comprising:
a neural interface component having:
a flexible substrate;
a plurality of independent, electrically conductive elements disposed on the substrate within a first region of the flexible substrate;
a plurality of electrically conductive traces formed on the flexible substrate, and in communication with the electrically conductive elements;
a plurality of electrically conductive interconnect pads formed in an array on the substrate within a second region, and being in communication with the plurality of electrically conductive traces;
an electronics module subsystem independent of the neural interface component, including:
a substrate;
an electronics circuit supported on the substrate;
a plurality of electrically conductive pads supported on the substrate and being in electrical communication with the electronics circuit, with the plurality of electrically conductive pads being configured in accordance with the plurality of the electrically conductive interconnect pads;
an independent interconnect subassembly configured to be positioned between the neural interface component and the electronics module subsystem, and to facilitate non-permanent electrically conductive connections between the plurality of electrically conductive interconnect pads and the electrically conductive pads when the second region of the neural interface component is aligned over the electrically conductive pads; and
a member for assisting in clamping the second region of the neural interface component and the independent interconnect subassembly adjacent the substrate of the electronics module subsystem.

13. The system of claim 12, wherein the independent interconnect subassembly comprises:
a non-electrically conductive substrate forming a planar component having opposing generally planar surfaces;
a plurality of electrically conductive wires embedded in the non-electrically conductive substrate such that the electrically conductive wires are exposed at both of the opposing generally planar surfaces, and operate to assist in making electrically conductive connections between the electrically conductive interconnect pads and the electrically conductive pads.

14. The system of claim 12, wherein the substrate of the neural interface component is formed from at least one of a flexible polymer or silicon.

15. The system of claim 12, wherein the system includes at least one of the following features:
the member for assisting in clamping the electrically conductive interconnect forms an independent component;
the member for assisting in clamping comprises at least one of a mechanical, chemical or magnetic feature; or
the member cooperates with an O-ring to seal a portion of the system from moisture ingress.

16. The system of claim 12, wherein the electronic circuit of the electronics module subsystem comprises a hermetically sealed subsystem.

17. The system of claim 12, wherein the electronic circuit includes at least one of:
a processor;
multiplexer;
an amplifier;
a battery;
a filtering circuit;
a memory;
a circuit for generating electrical stimulation signals for application to an anatomy; and
a wireless communications subsystem.

18. The system of claim 12, wherein the substrate of the electronics module subsystem further comprises an electrical connector in communication with the electronics circuit for receiving an external electrical communications cable.

19. A method for at least one of obtaining or generating electrical signals, the method comprising:
providing an interface component having a flexible substrate and a plurality of independent, electrically conductive elements disposed on the substrate in communication with a plurality of electrically conductive interconnect pads, also disposed on the substrate;
using the electrically conductive elements to at least one of receive the electrical signals when the interface component is placed in contact with matter being sensed, or to apply electrical signals to the matter;
releasably securing the electrically conductive interconnect pads of the interface component to a plurality of electrically conductive pads of an electronics module subsystem; and
using an electronic circuit contained in the electronics module subsystem to at least one of receive or generate the electrical signals.

20. The method of claim 19, further comprising placing an electrical interconnect subassembly between the electrically conductive pads and the electrically conductive interconnect pads, to assist in making electrical connections between the electrically conductive pads and the electrically conductive interconnect pads.

21. The method of claim 19, wherein using an electronics circuit to at least one of receive or to generate the electrical signals comprises using an electronics circuit including at least one of:
- a processor;
- a multiplexer;
- a filtering circuit;
- a memory;
- an amplifier;
- a battery;
- a circuit for generating electrical stimulation signals for application to the matter;
- an antenna for at least one of wireless data transmission or wireless power telemetry; and
- a wireless communications subsystem.

22. The method of claim 19, further comprising at least one of:
- coupling the electrical circuit to a connector to enable an external electrical communications cable to be interfaced to the electrical circuit; or
- supporting the electrically conductive pads and the electrical circuit on a common substrate, and hermetically sealing the electrical circuit.

\* \* \* \* \*